(12) United States Patent
Katarow

(10) Patent No.: US 6,643,531 B1
(45) Date of Patent: Nov. 4, 2003

(54) COMBINATION FINGERPRINT AND OXIMETRY DEVICE

(75) Inventor: Frank Katarow, Pewaukee, WI (US)

(73) Assignee: BCI, Inc., Waukesha, WI (US)

( * ) Notice: Subject to any disclaimer, the term of this patent is extended or adjusted under 35 U.S.C. 154(b) by 0 days.

(21) Appl. No.: 10/225,171

(22) Filed: Aug. 22, 2002

(51) Int. Cl.$^7$ ................................................ A61B 5/00
(52) U.S. Cl. ...................................... 600/344; 600/323
(58) Field of Search ................................ 600/310, 322, 600/323, 340, 344; 340/5.8, 5.82, 5.83; 382/115, 124

(56) References Cited

U.S. PATENT DOCUMENTS

| | | |
|---|---|---|
| 5,719,950 A | 2/1998 | Osten et al. |
| 5,876,926 A | 3/1999 | Beecham |
| 6,088,585 A | 7/2000 | Schmitt et al. |
| 6,094,589 A | 7/2000 | Schmitt |
| 6,141,436 A | 10/2000 | Srey et al. |
| 6,181,808 B1 | 1/2001 | Fukuzumi |
| 6,537,225 B1 * | 3/2003 | Mills ........................... 600/481 |
| 2002/0125991 A1 * | 9/2002 | Levin ........................... 600/323 |

* cited by examiner

*Primary Examiner*—Eric F. Winakur
(74) *Attorney, Agent, or Firm*—Louis Woo

(57) ABSTRACT

Incorporated to a finger grip device are an oximeter that measures the $SpO_2$ of the patient and a fingerprint sensor for sensing the fingerprint of the finger from which the $SpO_2$ is measured. The sensed fingerprint is used to identify the patient. By thus establishing the identity of the patient, the measured $SpO_2$ could readily be associated with the patient and appropriately displayed and stored, either at the patient site or remotely. The monitored data could also be readily associated with records of the patient and other physiological could data of the patient that may have been prestored in the controller to which the finger grip device is connected, or in a memory at a remote location. Mistakes in patient identification and the correspondence of wrong patient data to patients are thereby substantially reduced if not eliminated.

20 Claims, 5 Drawing Sheets

COMBINATION FINGERPRINT AND OXIMETRY DEVICE

FIELD OF THE INVENTION

The present invention relates to devices for monitoring the physiological attributes of a user and more particularly to a combination fingerprint and oximetry device that identifies or confirms the identity of the user as the oxygen saturation level of the arterial blood of the user is being monitored.

BACKGROUND OF THE INVENTION

The oxygen saturation in blood is monitored by oximeters. Some of these oximeters include BCI's 6200 and 6100 Series Vital Sign Monitors, and BCI's Capnocheck Plus, Autocorr Plus and Mini-Torr Plus monitors. In addition, there are a number of handheld pulse monitors including for example BCI's 3301 handheld pulse oximeter and 3301T Oxitemp Oximeter. The handheld oximeters are mainly used for on-spot checking of a patient, while the vital sign monitors are used to measure myriad physiological parameters of a patient which may then be transmitted to a remote location such as for example a nursing station or a doctor's office so that-the physiological parameters of the patient may be remotely monitored and analyzed. The fact that there are oftentimes a number of patients connected to separate vital sign monitors mean that there is a chance that the monitored parameters of a particular patient may be wrongly assigned to and be confused with another patient when displayed at the remote location. A system, and a device therefor, is therefore needed to ensure that patient outputs are correctly identified and assigned, particularly with being monitored pulse oximetry.

SUMMARY OF THE PRESENT INVENTION

To provide positive identification of a patient, the system of the instant invention includes a finger grip device that has incorporated therein both an oximeter and a fingerprint sensor. The finger grip device may be connected to a controller on which both graphic display and numeric display may be provided for indicating the measured or monitored oxygen saturation level of the blood of the patient. The controller may include a fingerprint circuit in addition to the oximeter circuit and other physiological circuitries such as ECG, $SpO_2$, pulse or heart rate, NIBP (Non-Invasive Blood Pressure), as well as temperature. The controller may also include a switch and a timer for controlling the activation of the fingerprint circuit, in relation to the oximeter circuit, so that a fingerprint scan of the finger of the patient may be activated for a brief period either before or after the oximeter circuit begins to measure the oxygen saturation in blood via the oximeter in the finger grip device. Alternatively, the activation of both the oximeter circuitry and the fingerprint circuitry may be done at the same time, and maintained on for the duration of the testing/monitoring. Further, the fingerprint sensor may be activated individually to obtain the fingerprint of a patient, which may be recorded in a memory, either in the controller or a remote memory store, or both.

To provide remote monitoring of the physiological parameters of a patient being measured, and specifically the oxygen saturation and the fingerprint of the patient, an optional display may be provided remotely from the controller such as for example at a nursing station or a doctor's office.

The controller further includes a communications port that enables it to be connected to a remote computer, for example the mainframe computer of the hospital to which the patient records are stored. Either by means of the controller, or by a separate fingerprint scanner connected to the remote computer, the fingerprint of a patient may be scanned and stored in the memory store of the remote computer, for identifying the patient and matching the patient with her records, medical or otherwise, and her other being measured physiological data, which may also be stored in the memory of the remote computer. As a consequence, for any real time measuring or monitoring of the physiological data of a patient, by means of the fingerprint data stored in the controller to which the finger grip device is connect and the remote mainframe computer, the being measured physiological data is readily matched to the appropriate patient, whose identity is confirmed via her fingerprint while her physiological data is being collected.

The connection of the finger grip device to the controller is by way of a conventional cable. However, it is envisioned that a short range wireless communications protocol, such as Bluetooth, may also be used, so that the finger grip device does not need to be physically tethered to the controller.

It is therefore an objective of the present invention to provide a patient monitoring system that includes a finger grip device that has incorporated therein both an oximeter and a finger print sensor.

It is another objective of the present invention to use, by means of the sensed or scanned fingerprint of the patient, as her $SPO_2$ is being measured, to identify the patient, so that both the being measured physiological data and any previously stored records of the-patient can be correlated or matched to the patient.

BRIEF DESCRIPTION OF THE FIGURES

The above-mentioned objectives and advantages of the instant invention will become apparent and the invention itself will be best understood by reference to the following description of embodiments of the invention taken in conjunction with the accompanying drawings, wherein.

DETAILED DESCRIPTION OF THE INVENTION

Figure 1:
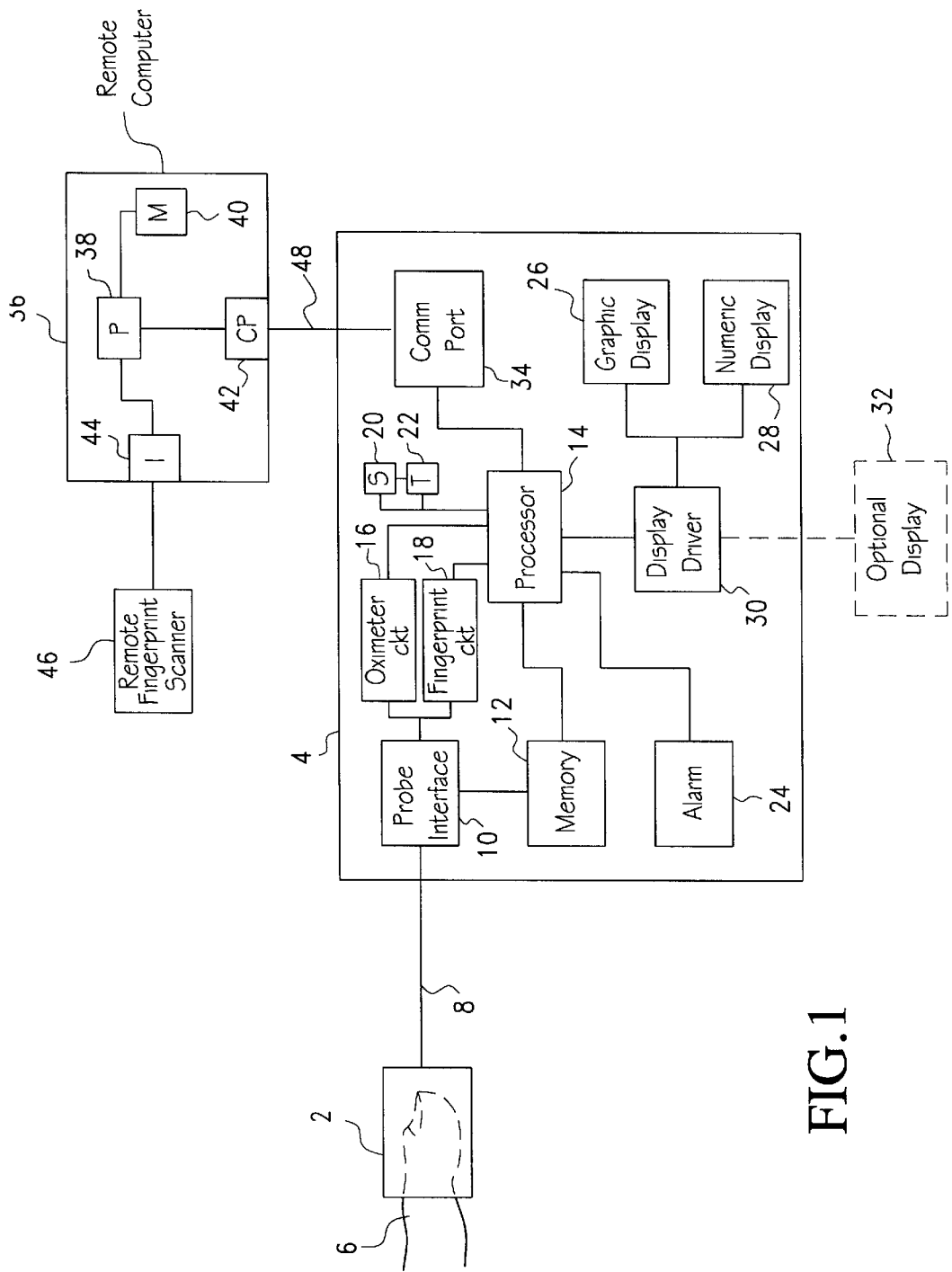
FIG. 1 is an overall view of the system of the instant invention.
Figure 2A:
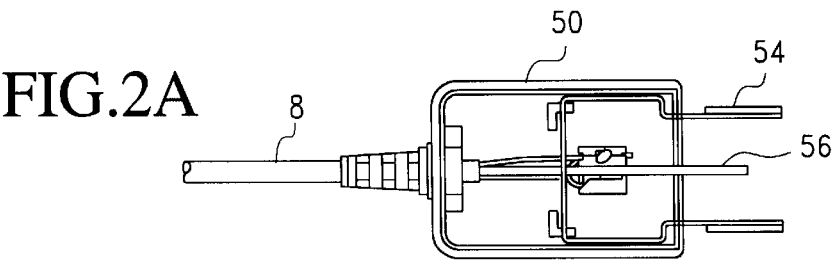
FIG. 2a is a top view of a top or upper portion of a finger grip device.
Figure 2B:
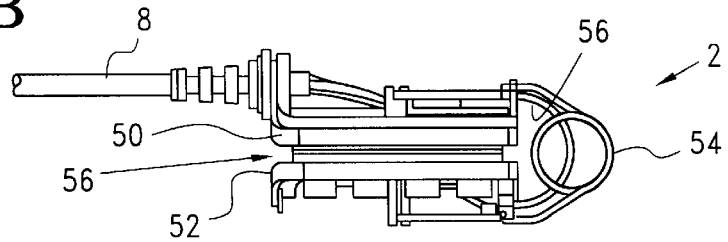
FIG. 2b is a side view of the finger grip device.

With reference to FIG. 1, the instant invention system includes a finger grip device 2 that is connected to a controller 4. The finger grip device may have the dimensions of one of the conventional finger grip devices being sold by the BCI company, and is configured to allow the insertion of a finger 6 therein so that the physiological data from the patient may be measured or monitored. Finger grip device 2 is shown to be electrically connected to controller 4 by means of a cable 8. It should be noted, however, that cable 8 may be replaced by a wireless connection with the appropriate communications protocol, such as for example Bluetooth, between finger grip device 2 and controller 4.

For the instant invention, however, cable 8 is connected to controller 4 by means of a probe interface 10. Probe interface 10 is an input/output port through which data may traverse between finger grip device 2 and controller 4. Probe interface 10 is connected to a memory 12 whereat, among other things, the scanned fingerprint of a patient may be stored for identification purposes. Memory 12 also stores the data collected from the oximeter portion of finger grip device 2, as well as other physiological parameters collected from the patient by other probes or sensors that may also be connected to the controller. Memory 12 is connected to a processor, for example a conventional microprocessor 14.

Connected to probe interface 10 are a number of circuits, including for example an oximeter circuit 16 and a fingerprint circuit 18. The oximeter circuit 16 may be a circuit that is provided in the various BCI devices such as for example the aforenoted BCI 6200 and 6100 Series Vital Signs Monitor, and the BCI Capnocheck Plus, Autocorr Plus and Mini-Porr Plus devices. Specific reference of the oximeter circuit 16 may also be gleaned from co-pending application Ser. No. 09/940,418 filed Aug. 29, 2001 and assigned to the same assignee as the instant invention. The disclosure of the '418 application including in particular the schematic directed to the oximeter circuit is incorporated by reference to the instant specification. The fingerprint circuit 18 may be a conventional fingerprint scan circuit disclosed for example in U.S. Pat. No. 5,852,670. The disclosure of the '670 patent is incorporated by reference herein.

There is also a switch 20 and a timer 22 provided in controller 4. Both of switch 20 and timer 22 are controllable by the user so that the fingerprint sensor and the oximeter provided in device 2 may be selectively controlled. More on that later. The controller further includes an alarm 24 for providing an indication of potential problems when a particular measurement of a patient has exceeded or fallen below acceptable upper and lower thresholds, respectively.

The measured data from the patient may be displayed both graphically by means of a graphic display 26 and numerically by means of a numeric display 28. The displays are driven by a display driver 30, which is connected to processor 14. Display driver 30 is also adaptable to drive an optional display 32 that ordinarily is not a part of controller 4. Such optional display 32 may be a monitor provided at a location such as a central nursing station that is remote from the patient's room whereat controller 4 is located.

Controller 4 further has a communications port 34 that allows it to telecommunicate with remote devices such as for example a remote computer of a hospital where the patient's records may be located. Such remote computer is represented by mainframe computer 36, which includes a processor 38 having electrically connected thereto a memory store 40. It is in memory store 40 that the various records of the many patients of the hospital, including the patient that is being monitored, may be stored. A communications port 42 at remote computer 36 acts as a transceiver for exchanging data between computer 36 and controller 4.

The mainframe computer may also be provided with an interface 44 that enables it to communicate with a remote fingerprint scanner 46. Scanner 46 provides the means whereby the hospital can scan in the fingerprints of its patients for identification purposes, so that the respective records stored in memory 40 may be matched to the corresponding patients whose fingerprints are stored in memory store 40. The connection between remote computer 36 and controller 4, designated by communication link 48, may be hardwired, telephonic, wireless or via the internet.

Figure 3:
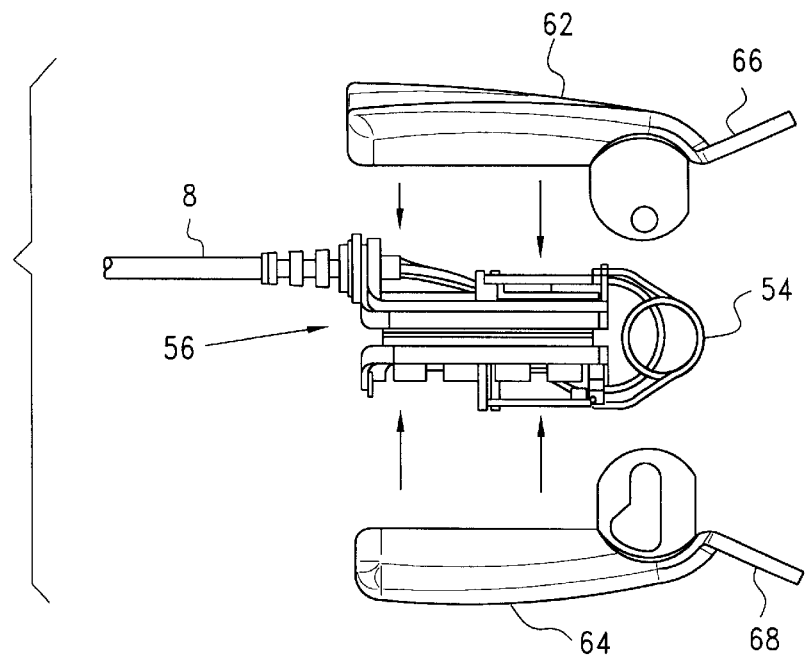
FIG. 3 is another side view of the instant invention finger grip device, with respective upper and lower covers being shown removed from the upper and lower portions.
Figure 4:
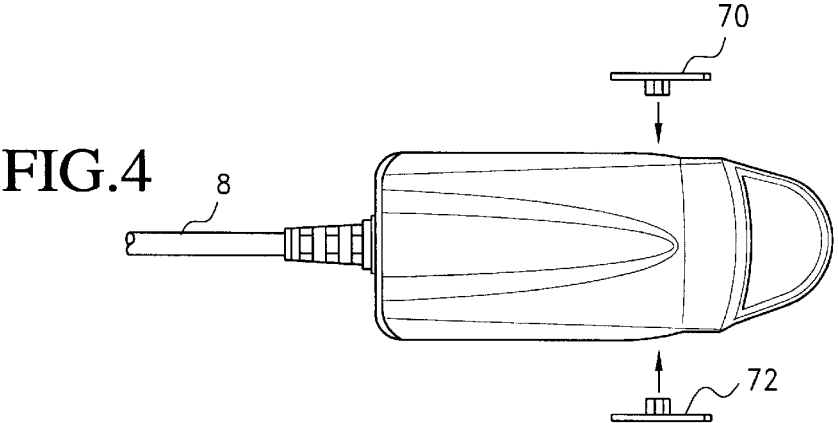
FIG. 4 is a top view of the finger grip device with the upper finger grip being shown to have mounted to the finger grip device.
Figure 5:
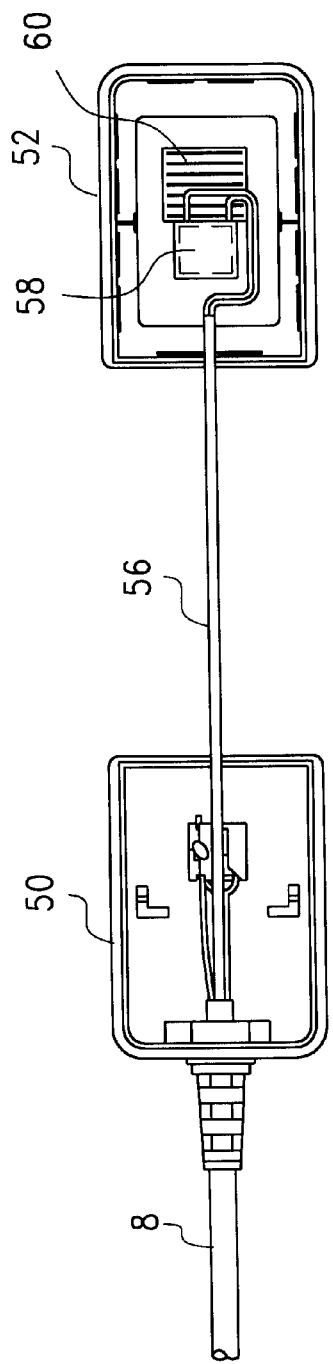
FIG. 5 is a plan view of the upper and lower finger grip portions of the finger grip device, with the oximeter sensor and fingerprint sensor shown.
Figure 6:
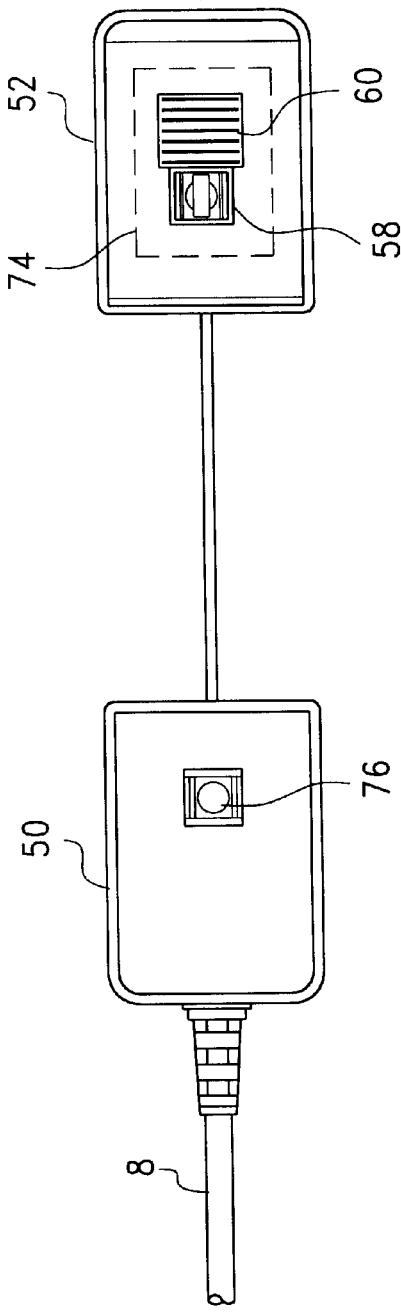
FIG. 6 is a reverse plan view of the finger grip portions of the device showing the respective windows at the upper and lower finger grip portions through which the oxygen saturation level and the finger print of a patient may be obtained.

FIGS. 2–6 illustrate in detail the finger grip device 2. In particular, device 2 is shown to have a first or upper finger grip portion 50 and a second or lower finger grip portion 52. As best shown in FIGS. 2b and 3, the finger grip portions 50 and 52 for the embodiment of the finger grip device shown in those figures is hingedly held by spring 54, so that when a finger is moved along the direction of directional arrow 56 and makes contact with finger grip portions 50 and 52, those portions are hingedly moved relative to each other to accommodate the incoming finger.

Upper and lower finger grip portions 50 and 52 are connected by a wire 56 that powers the oximeter detector 58 and the fingerprint sensor 60 provided at finger grip portion 52. Covers 62 and 64 are provided to finger grip portions 50 and 52, respectively, per shown in FIG. 3. Handles 66 and 68 of covers 62 and 64, respectively, enable a user to open finger grip portions 50 and 52 relative to each other to ease the insertion of the finger of the user between the finger grip portions. Covers 62 and 64 are held to the finger grip portions by inserts 70 and 72, as shown in the top view of the device in FIG. 4. To expose the finger pad of the inserted finger to the fingerprint sensor 60 and the oximeter detector 58, a window 74 is provided at finger grip portion 52. Window 74 is of a dimension sufficient to ensure that sufficient portion of the finger pad is exposed to the fingerprint sensor so that the fingerprint of the user could be sensed.

Figure 7:
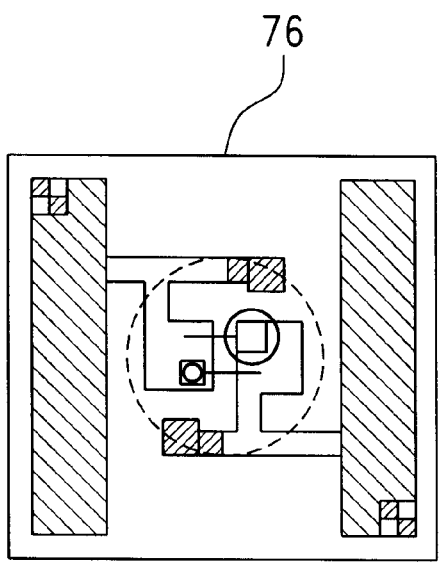
FIG. 7 is a plan view of a light source for the oximeter of the finger grip device of the instant invention.

A light source 76 is provided at finger grip portion 50 to produce a light detected by photodetector 58 of the oximeter. The conventional light source is made up of at least two LEDs, as shown in FIG. 7. The operation of the oximeter of the instant invention for obtaining the $SPO_2$ of the patient is similar to the operation performed by the aforenoted BCI oximeters, and is also disclosed in the aforenoted application Ser. No. 09/940,418.

Figure 8:
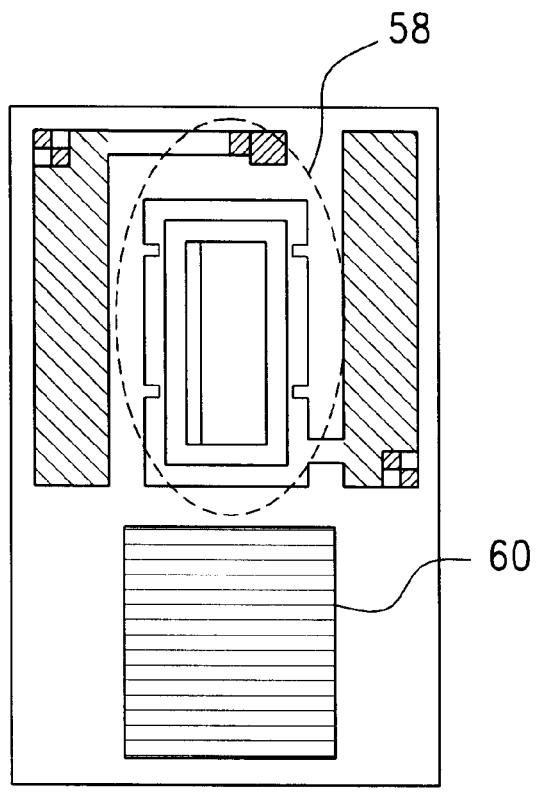
FIG. 8 is a detector portion that incorporates both the oximeter detector and the fingerprint sensor of the instant invention.

As best shown in FIG. 8, in addition to photodetector 58 of the oximeter, the lower finger grip portion 52 of finger grip device 2 has a fingerprint sensor. Such fingerprint sensor is conventional and is disclosed for example in U.S. Pat. No. 4,429,413, the disclosure of which being incorporated by reference herein. In essence, fingerprint sensor 60 has an array of sensing cells, each including a transistor having a gain that depends on the pressure/temperature variations existing at the surface of the ball or pad of the finger that is making contact therewith. Sensor 60 converts the fingerprint at the ball of the finger into a topological pattern that is unique to the particular finger of the user. Although shown to be adjacent to each other, photodetector 58 and fingerprint sensor 60 may be arranged to complement each other to optimize the footpad of the finger grip device 2.

In operation, when a patient or user inserts her finger to device 2, depending on whether the patient's fingerprint had previously been stored, the nurse or physician in charge of controller 4 may selectively activate switch 20 and set timer 22 such that the fingerprint of the patient is sensed, before the patient's $SPO_2$ is measured. By scanning the patient's fingerprint first, the fingerprint of the patient may be routed by controller 4 to the mainframe computer 36 to identify the patient and to match the patient with the later collected data, which could then be stored in the appropriate file in remote memory store 40 that is associated with the patient. As was mentioned previously, the scanned fingerprint of the patient may also be stored in memory 12 of controller 4.

Once the patient is identified, the $SpO_2$ of the patient, as it is being measured, is displayed at controller 4, and also possibly at optional display 32, with the patient's identity associated with the particular display.

The fingerprint sensor may also be operated periodically, in accordance with a specific setting of the timer 22 and switch 20, so that periodic reading of the fingerprint of the patient is taken to ensure that the being monitored physiological data continues to correspond to the same patient. Also, the fingerprint sensor may be turned on continuously, and simultaneously, with the operation of the oximeter, so that continuous readings of the patient's $SPO_2$ and fingerprint take place. As noted earlier, by associating the being collected physiological data with the identity of the patient, the collected data could readily be associated with previous collected data for that patient, so that the being collected data could be added to the previously stored data. Further, by identifying the patient every time that a physiological data such as for example the $SpO_2$ of the patient is collected, the chances of a patient identification error occurring are reduced.

In the event that the remote computer requires that particular records stored in memory 40 be related to a patient before any tests for the patient are performed, the remote fingerprint scanner 46 connected to the remote computer may be used to sense the fingerprint of the patient, so that the identity of the patient is preestablished in the remote computer. By thus preestablishing the identify of a patient, as the patient's $SPO_2$, and other physiological data, is collected by finger grip device 2 and other probes coupled to the patient remote from mainframe computer 36, the data collected and processed by controller 4 could readily be routed to remote computer 36, and matched to the patient for storage and analysis remotely from the patient.

Figure 9:
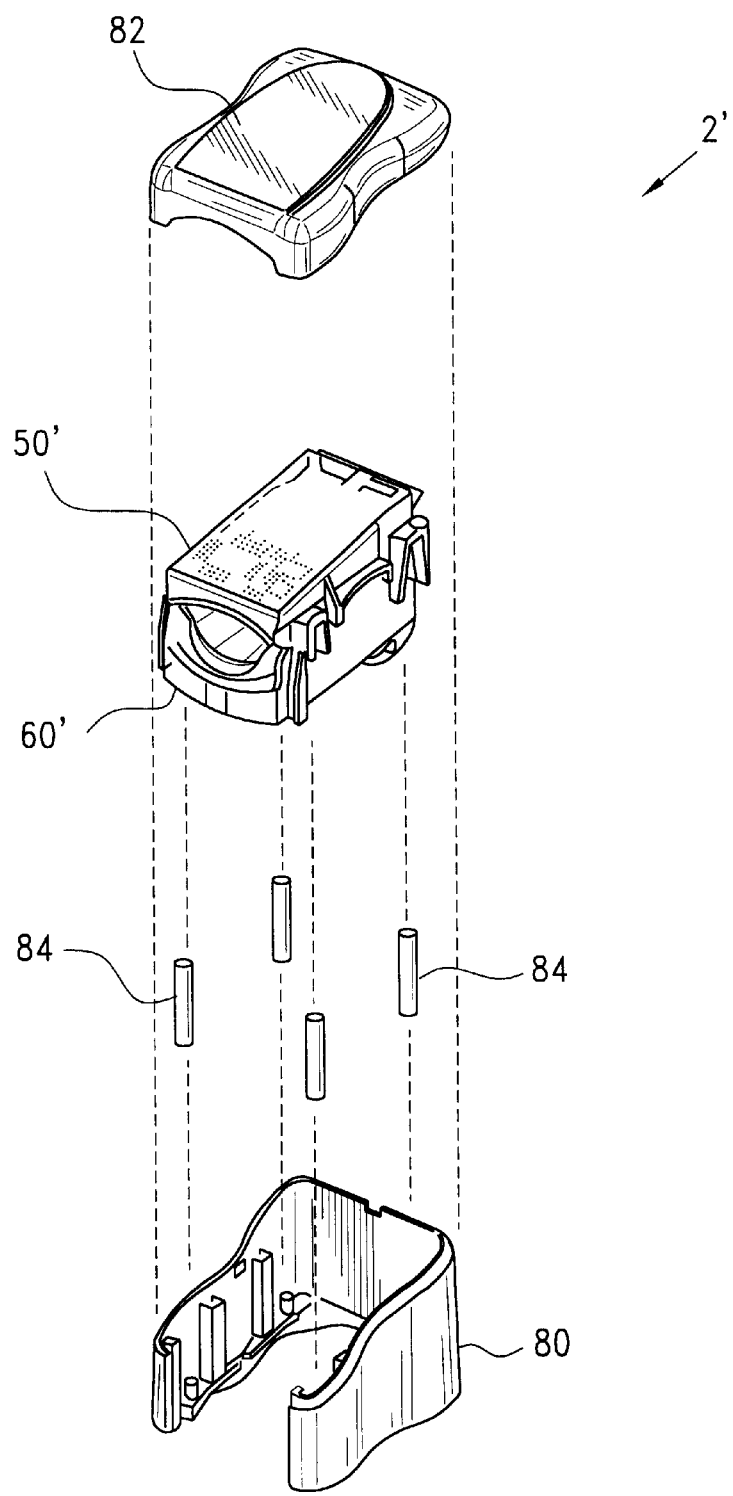
FIG. 9 is a perspective view of another embodiment of the finger grip device in which the upper and lower finger grip portions are held by a floating suspension system.

FIG. 9 is an exploded view of another embodiment of the finger grip device 2 in which the finger grip portions 50' and 60' are housed in a casing 80, with upper finger grip portion being fixedly held to casing 80 by a cover 82. The movement of upper portion 50' relative to lower portion 60' is supported by a plurality of springs 84, which act as a suspension system for lower finger grip portion 60' when it moves in a vertical direction relative to upper finger grip portion 50'. The detailed operation of such suspension system is provided in the aforenoted incorporated by referenced application Ser. No. 09/940,418.

The present invention is subject to many variations, modifications and changes in detail. Thus, it is intended that all matter described throughout this specification and shown in the accompanying drawings be interpreted as illustrative only and not in a limiting sense. Accordingly, it is intended that the invention be limited only by spirit and scope of the hereto appended claims.

What is claimed is:

1. In combination, a first finger portion and a second finger portion movable relative to each other, the respective surfaces of the finger portions configured to conform to a finger placed therebetween by a user, a light source provided at one of the finger portions and a light detector provided at the other of the finger portions for forming a finger pulse oximeter, the oxygen saturation of the arterial blood of the user being monitored by said finger pulse oximeter, and a fingerprint sensor provided at one of said finger portions for sensing the fingerprint of the finger placed between said finger portions.

2. The combination of claim 1, wherein said light detector of said pulse oximeter and said fingerprint sensor are mounted to the same finger portion.

3. The combination of claim 2, further comprising:

a window provided on the finger portion where said fingerprint sensor and said light detector of said pulse oximeter are mounted, said window being of a sufficient size to enable the sensing of the fingerprint of the finger placed between said finger portions.

4. The combination of claim 1, further comprising:

a controller connected to said finger portions via an electrical connection, said controller including switch means for selectively activating said finger pulse oximeter and/or said fingerprint sensor.

5. The combination of claim 1, wherein said pulse oximeter and said fingerprint sensor may be activated simultaneously, individually, or with different on/off periods.

6. The combination of claim 1, wherein the fingerprint of the user is prestored in a memory remote from said finger portions; and wherein the fingerprint sensed from the user is associated with the blood oxygen saturation monitored by said pulse oximeter and compared with the prestored fingerprint of the user to ensure that the blood oxygen saturation level being monitored is that of the user.

7. Apparatus, comprising:

a housing wherein to a finger of a user is positioned, said housing having an upper portion and a lower portion;

a light source and a sensor for detecting light from said light source mounted to said upper and lower portions, respectively, for effecting a pulse oximeter; and a fingerprint sensor mounted to said lower portion in cooperation with said pulse oximeter.

8. Apparatus of claim 7, further comprising:

a controller separate from but electrically connected to said housing for receiving the respective signals output from said pulse oximeter and said fingerprint sensor.

9. Apparatus of claim 8, wherein said controller comprises:

at least one signal processor for processing the respective signals received from said pulse oximeter and said fingerprint sensor; and a transceiver for routing the received signals to a remote station whereat the sensed fingerprint is compared with a prestored fingerprint of the user to confirm that the sensed fingerprint is from the same user, and to associate the monitored blood oxygen saturation with the confirmed user.

10. Apparatus of claim 9, further comprising:

a monitor remote from said housing for displaying the monitored blood oxygen saturation level of the confirmed user.

11. Apparatus of claim 7, further comprising:

a controller connected to said finger portions via an electrical connection, said controller including switch means for selectively activating said finger pulse oximeter and/or said fingerprint sensor.

12. Apparatus of claim 7, wherein one of said upper and lower portions is spring biased vertically relative to the other.

13. Apparatus of claim 7, further comprising a window provided on said lower portion, said window being of a sufficient size to enable the sensing of the fingerprint of the finger placed between said upper and lower portions.

14. Apparatus of claim 7, wherein said pulse oximeter and said fingerprint sensor may be activated simultaneously, individually, or with different on/off periods.

15. A combination finger oximeter and fingerprint device, comprising:

a first finger grip portion;

a second finger grip portion in opposed relationship to said first finger grip portion;

a light source mounted to said first finger grip portion;

a light detector mounted to said second finger grip portion;

a sensor mounted to said second finger grip portion in cooperation with said light detector;

wherein said light detector and light source in combination form an oximeter for monitoring the oxygen saturation of the blood of a user whose finger is gripped by said first and second finger portions; and wherein said sensor senses the fingerprint of the finger gripped by said first and second finger grip portions so that the sensed fingerprint can be used to identify the user whose blood oxygen saturation is being monitored.

16. The device of claim 15, further comprising:

an electrical connection connecting said device to a controller, said controller including switch means for selectively activating said finger oximeter and/or said fingerprint sensor.

17. The device of claim 15, wherein said oximeter and said fingerprint sensor may be activated simultaneously, individually, or with different on/off periods.

18. The device of claim 15, wherein the fingerprint of the user is prestored in a memory remote from said device; and wherein the fingerprint sensed from the user is associated with the blood oxygen saturation being monitored by said oximeter and compared with the prestored fingerprint of the user to confirm the being monitored blood oxygen saturation is from the user.

19. The device of claim 15, further comprising:

a window provided on said second finger grip portion, said window being of a sufficient size to enable the sensing of the fingerprint of the finger placed between said first and second finger grip portions.

20. The device of claim 15, further comprising:

an electrical connection to a controller remote from said device for receiving the respective signals output from said oximeter and said fingerprint sensor, said controller including at least one signal processor for processing the respective signals received from said oximeter and said fingerprint sensor and displaying the processed signals on a display.

* * * * *